Jan. 15, 1946. F. ROURKE Plant Pat. 671
VIOLA PLANT
Filed Jan. 23, 1945
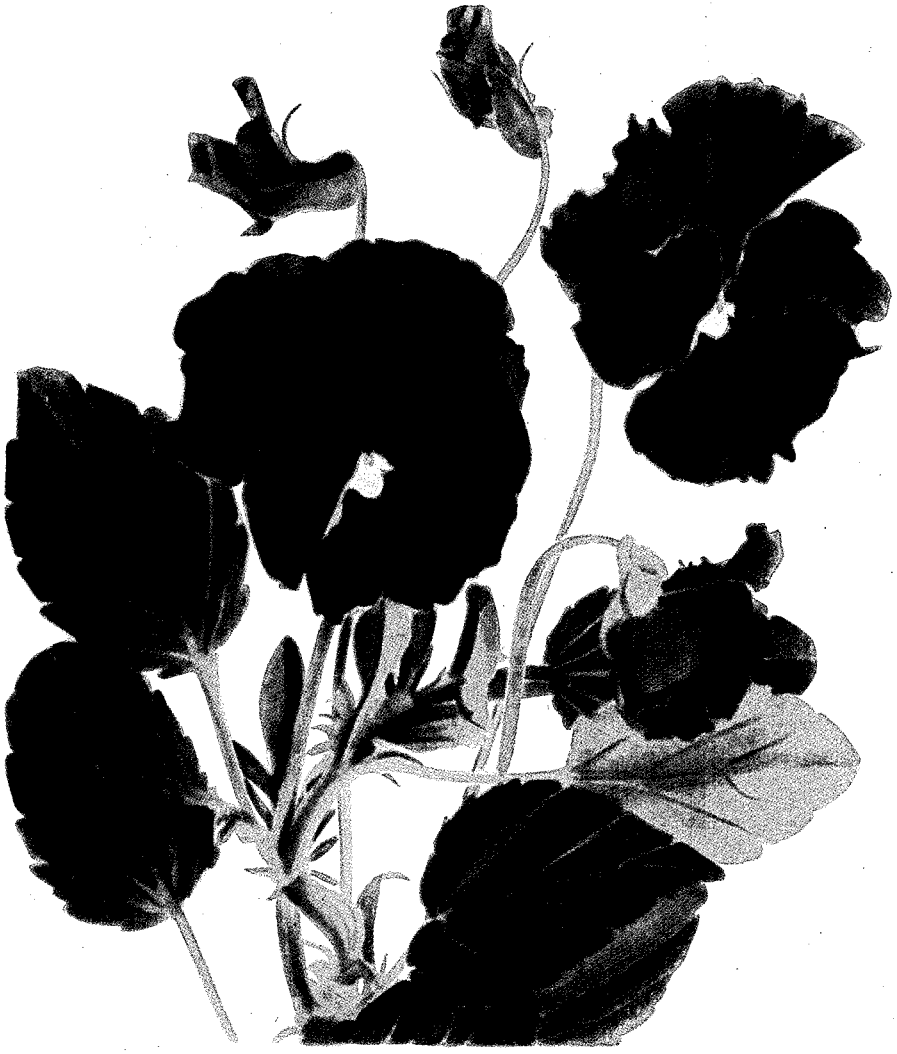
Inventor
Frank Rourke
By Robb & Robb
His Attorneys Patented Jan. 15, 1946

Plant Pat. 671

UNITED STATES PATENT OFFICE

671

VIOLA PLANT

Frank Rourke, Westfield, Mass., assignor to Jackson & Perkins Company, Newark, N. Y., a corporation of New York Application January 23, 1945, Serial No. 574,104

1 Claim. (Cl. 47—60)

The present invention relates to a new and distinct variety of viola plant, originated by the crossing of the two varieties "Beauty of Larone" and "Viola Jersey Gem."

The variety belongs to the class of hardy ever-blooming perennials particularly useful for both garden decoration and cut flower purposes, especially having in mind the novel color of the blooms.

In addition to the valuable and attractive features above referred to, the new viola is characterized as to novelty by its large size flowers grown on very long stems—seven or eight inches in length—very unusual for perennial violas. This long stem feature differentiates the present variety from its parent "Beauty of Larone," and the large flower and long creeping shoots distinguish the new variety from its parent "Viola Jersey Gem."

By combining in this new variety these important characteristics, a much desired and valuable improvement from the commercial standpoint has been produced.

Furthermore, the new variety is very resistant to frost, flowers being found even in the snow as late as December.

Asexual reproduction shows that these characteristics hold true through succeeding propagations.

The following is a detailed description of this new variety, color terminology being in accord with Ridgeway's color standard:

Parentage: Seedling.
*Seed parent.*—"Beauty of Larone."
*Polen parent.*—"Viola Jersey Gem."
Classification:
*Botanic.*—Viola Cornuta Hybrid.

*Flower*

(Observations made in the fields of Jackson & Perkins Company, Newark, New York, in the morning of October 5, 1944.)

Blooming Habit: Recurrent—continuous.
Bud:
*Size.*—Large.
*Color.*—When sepals first divide—Hyacinth Violet, Plate 11; when petals being to unfurl—upper part of petal, Hyacinth Violet, Plate 11; center, Mulberry Purple, Plate 11. When half blown—inside of petals, Blackish Purple, Plate 11; reverse of petals, Litho Purple, Plate 25.
*Sepals.*—Branched, 5. *Color*—Biscay Green, Plate 17.
Bloom:
*Size.*—Very large. Average size, when fully expanded, 3–3¼ inches in length; 2½ inches in width.
*Stems.*—Long; 7–8 inches; strong. *Color*—Rainette Green, Plate 31.
*Petalage.*—5 petals; thick; not affected by wet or hot weaher; velvety inside and shiny outside.
*Color.*—Two upper petals, Cotinga Purple, Plate 11, overlaid with Pansy Violet, Plate 11; large and fluted. Two side petals, Mulberry Purple, Plate 11, with an overcast of Pansy Violet, Plate 11; prominent veins of a Mulberry Purple, Plate 11; base of the two side petals forming part of the eye, Sea Foam Yellow, Plate 31. Lower petal, Mulbery Purple, Plate 11, with an overcast of Pansy Violet, Plate 11, more prominently veined in Mulberry Purple, Plate 11, than the two side petals. Reverse, Litho Purple, Plate 25.
Fragrance: Moderate viola fragrance.
Lasting Quality: On plant and as cut flower—very long.
Form: Vigorous growing; has a tendency to send out long runners.
Growth: Vigorous.
Foliage:
*Color.*—Upper side, Yew Green, Plate 31; lower side, Rainette Green, Plate 31.
*Shape.*—Ovate; petiolate; coming from nodes on the stem which are marked with fern-like leaflets. These nodes also produce the flower stem.
*Veins.*—Pennately veined with regular crenate serations.

I claim:

A new and distinct variety of Viola Plant characterized as to novelty by the color and large size of the flowers grown on unusually long stems, its habit of putting out long creeping shoots and its high resistance to frost, substantially as shown and described.

FRANK ROURKE.